(12) United States Patent
Ettema et al.

(10) Patent No.: US 7,902,198 B2
(45) Date of Patent: Mar. 8, 2011

(54) CRYSTALLINE ARIPIPRAZOLE SOLVATES

(75) Inventors: Gerrit Jan Ettema, Nijmegen (NL); Raymond Westheim, Nijmegen (NL); Faysal Kalmoua, Oss (NL)

(73) Assignee: Synthon BV, Nijmegen (NL)

( * ) Notice: Subject to any disclaimer, the term of this patent is extended or adjusted under 35 U.S.C. 154(b) by 1049 days.

(21) Appl. No.: 11/281,498

(22) Filed: Nov. 18, 2005

(65) Prior Publication Data

US 2006/0142299 A1    Jun. 29, 2006

Related U.S. Application Data

(60) Provisional application No. 60/628,654, filed on Nov. 18, 2004.

(51) Int. Cl.
  *A61K 31/497* (2006.01)
  *C07D 401/00* (2006.01)
(52) U.S. Cl. .................................. 514/253.08; 544/363
(58) Field of Classification Search ............. 514/253.08; 544/363
  See application file for complete search history.

(56) References Cited

U.S. PATENT DOCUMENTS

| 3,177,820 A * | 4/1965 | Wiley et al. ................. 425/72.1 |
| 4,734,416 A | 3/1988 | Banno et al. |
| 5,006,528 A * | 4/1991 | Oshiro et al. ............ 514/253.07 |
| 2004/0058935 A1 | 3/2004 | Bando et al. |
| 2006/0142299 A1 * | 6/2006 | Ettema et al. ............ 514/253.07 |

FOREIGN PATENT DOCUMENTS

| EP | 367141 | | 1/1996 |
| WO | WO 03/026659 | | 4/2003 |
| WO | WO 2005/009990 | * | 2/2005 |
| WO | WO 2005/058835 A2 | | 6/2005 |

OTHER PUBLICATIONS

Gatterman, Ludwig, "The Practical Methods of Organic Chemistry," 1896, MacMillan: New York, pp. 1-14.*
Grady MA, Gasperoni TL, and Kirkpatrick P, "Aripiprazole," Nature Reviews Drug Discovery, Jun. 2003, 2, 427-428.*
Kelleher JP, Centorrino F, Albert MJ, and Baldessarini RJ, "Advances in atypical antipsychotics for the treatment of schizophrenia: new formulations and new agents," CNS Drugs, 2002, 16(4), 249-261.*
Vippagunta SR, Brittain HG, and Grant D J, "Crystalline solids," Advanced Drug Delivery Reviews, May 2001,48(1), 3-26.*
Morissette SL, Almarsson O, Peterson ML, Remenar JF, Read MJ, Lemmo AV, Ellis S, Cima MJ, and Gardner CR, "High-throughput crystallization: polymorphs, salts, co-crystals and solvates of pharmaceutical solids," Advanced Drug Delivery Reviews, Feb. 2004, 56(3), 275-300.*
"Study on Crystal Transformation of Aripiprazole" The Fourth Japan-Korea Symposium on Separation Technology (1996), pp. 937-940.

* cited by examiner

*Primary Examiner* — San-ming Hui
*Assistant Examiner* — Paul Zarek
(74) *Attorney, Agent, or Firm* — Muncy, Geissler, Olds & Lowe, PLLC

(57) ABSTRACT

Alcoholates of aripiprazole are useful as pharmaceuticals and/or as intermediates in making aripiprazole Form A or Form B.

16 Claims, 6 Drawing Sheets

IR spectrum of hemi-ethanolate (Example 3)

XRPD spectrum of hemi-ethanolate (Example 3)

NMR spectrum of hemi-ethanolate (Example 3)

DSC scan of hemi-ethanolate (Example 3)

TGA curve of hemi-ethanolate (Example 3)

XRPD spectrum of methanolate (Example 6)

IR spectrum of methanolate (Example 6)

NMR spectrum of methanolate (Example 6)

DSC scan of methanolate (Example 6)

TGA curve of methanolate (Example 6)

CRYSTALLINE ARIPIPRAZOLE SOLVATES

This application claims the benefit of priority from U.S. Provisional Application 60/628,654, filed Nov. 18, 2004, the entire contents of which are incorporated herein by reference.

BACKGROUND OF THE INVENTION

The present invention relates to crystalline solvates of 7-[4-[4-(2,3-dichlorophenyl)-1-piperazinyl]butoxy]-3,4-dihydrocarbostyril, also known as aripiprazole and to the making and using of the same.

Aripiprazole is a compound of the formula (1).

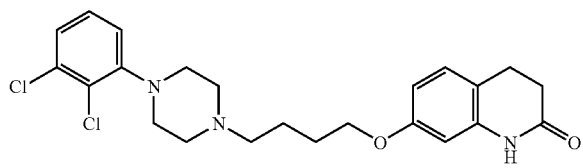

(1)

It is a commercially marketed, pharmaceutically active substance useful for treatment of schizophrenia. It is disclosed in EP 367141/U.S. Pat. No. 5,006,528. The commercially marketed product contains the compound (1) as the free base; i.e., not as an aripiprazole salt.

Solid state aripiprazole was prepared in U.S. Pat. No. 5,006,528 by a two-fold recrystallization of crude aripiprazole from ethanol resulting in colorless flake crystals having a melting point of 139-139.5° C. In an article of Aoki (Study on Crystal Transformation of Aripiprazole, The Fourth Japan-Korea Symposium on Separation Technology, p. 937 ff (1996)), this solid state form was designated as Type I aripiprazole and identified as an anhydrate. Aoki also teaches that the Type I aripiprazole may be converted into a Type II aripiprazole by heating at 130-140° C. for 15 hours. This product is an anhydrate as well with a melting point of 150° C. When both Type I and Type II aripiprazole were recrystallized from an alcoholic solvent containing water up to 20%, the product was an aripiprazole hydrate labeled as Type III by Aoki. Type III aripiprazole can be converted into the Type I by heating at 80° C.

WO 03/26659 (EP 1330249) teaches that Type I aripiprazole, the alleged original solid form of aripiprazole, is significantly hygroscopic. In an effort to find a form of aripiprazole having reduced hygroscopicity and better processing qualities, seven crystalline forms (A-G) were described.

Hydrate Form A is taught as a useful intermediate for making anhydrate forms. Hydrate Form A can be prepared by milling Aoki's hydrated Type III.

Anhydrous Form B, which seems to be the preferred crystalline form, is not hygroscopic; i.e., less than 0.4% water uptake in 24 hours, and is a stable crystalline form. It can be prepared by heating the Hydrated Form A, preferably at 90-125° C. for 3-50 hours or by heating the Type I/Type II aripiprazole at 90-125° C.

The other anhydrate forms disclosed therein are briefly summarized below.

Form C: Prepared by heating an aripiprazole anhydrate to 140-150° C. Endothermic peak around 150.2° C.

Form D: Prepared by recrystallization of aripiprazole anhydrate from toluene. Endothermic peaks at 136.8 and 141.6° C.

Form E: Prepared by double heating, dissolving, and crystallizing aripiprazole in acetonitrile with crystallization at about 70° C. Endothermic peak at 146.5° C.

Form F: Prepared by heating a suspension of aripiprazole anhydrate in acetone. Endothermic peaks at 137.5 and 149.8° C.

Form G: Prepared by putting glassy state of aripiprazole anhydrate in a sealed vessel and keeping it at room temperature for at least 2 weeks. Exothermic peak at 122.7° C., endothermic peak at 141.0° C.

In particular, it would be desirable to find other crystalline forms of aripiprazole, particularly preparable in a reliable process on an industrial scale. Furthermore, it would be desirable to find alternate processes for making useful crystalline forms of aripiprazole, especially Form B aripiprazole.

SUMMARY OF THE INVENTION

The present invention is based on the discovery that aripiprazole may form crystalline solvates with methanol or ethanol (alcoholates). Accordingly, a first aspect of the invention relates to an alcoholate of aripiprazole selected from aripiprazole hemi-ethanolate and aripiprazole methanolate. The alcoholates can be used as pharmaceutical active agents such as in a pharmaceutical composition with at least one pharmaceutically acceptable excipient. In some embodiments, the aripiprazole alcoholate is granulated with a granulateable binder to form pharmaceutical granules.

Alternatively, another aspect of the present invention relates to a process for making aripiprazole Form B, which comprises heating an aripiprazole alcoholate selected from aripiprazole hemi-ethanolate and aripiprazole methanolate to form aripiprazole Form B.

The solvates may be prepared by crystallization of aripiprazole from methanol or ethanol, respectively. Specifically, in one aspect the invention relates to a process for making aripiprazole hemi-ethanolate, which comprises providing a solution of aripiprazole in ethanol; crystallizing aripiprazole from the solution; and drying the crystals to have a bound solvent content within the range of about 0.4 to 0.6 moles per mole of aripiprazole. In another aspect, the invention relates to a process for making aripiprazole methanolate, which comprises providing a solution of aripiprazole in methanol; and crystallizing aripiprazole methanolate from said solution.

DETAILED DESCRIPTION OF THE INVENTION

Figure 1:
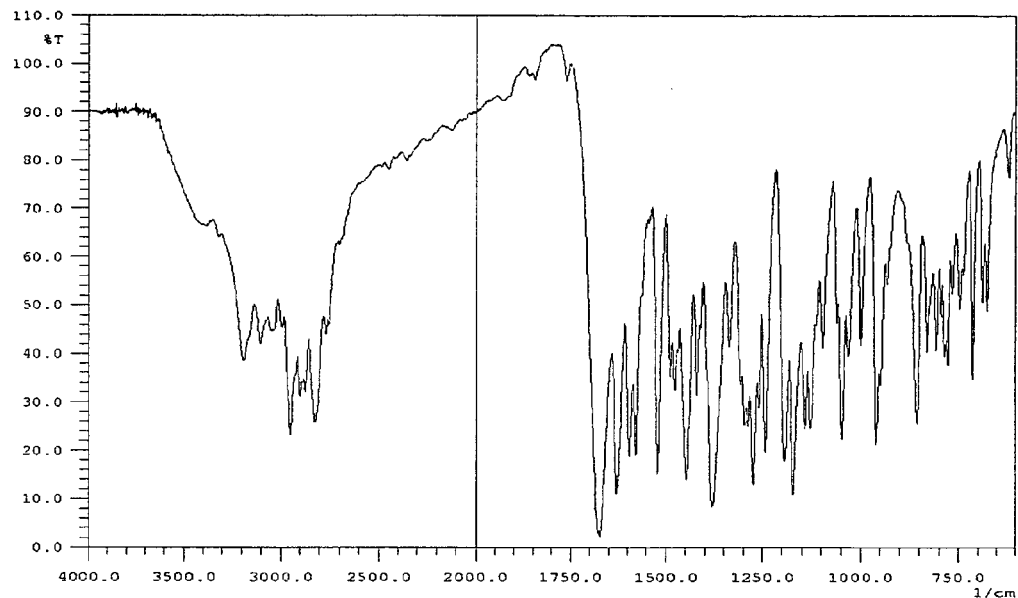
FIG. 1 represents an IR spectrum of aripiprazole hemi-ethanol solvate of Example 3.

The present invention is based on a finding that aripiprazole may be isolated, in solid state, in a form of a crystalline solvate with ethanol or methanol. Both solvates may be used per se as a pharmaceutical substance or, advantageously, may be converted into a solvent-free aripiprazole, particularly into Form B aripiprazole. The conversion can be carried out by heat treatment or by recrystallization from a solvent selected from 1-propanol, 2-propanol, 1-butanol, ethyl acetate, acetonitrile, or combination thereof. They also may be converted into a hydrated aripiprazole such as Form A aripiprazole, by a crystallization from a solvent comprising water.

The ethanol solvate is isolateable as essentially an aripiprazole hemi-ethanolate. The chemical structure of aripiprazole hemi-ethanolate is characterized in that it comprises essentially half molar amount of ethanol per molar amount of aripiprazole. Preferably, the isolated product is free from unbound solvent. In practice, the molar ratio between aripiprazole and ethanol moieties in the isolated product is from 1:0.4 to 1:0.6, preferably 1:0.45 to 1:0.6. It is a crystalline substance having a specific IR spectrum and x-ray powder diffraction pattern different from any other known crystalline form of aripiprazole, thus indicating that the compound is a real solvate. This feature is supported by analyzing the product by DSC or thermogravimetry. Aripiprazole hemi-ethanolate is reasonably stable upon storage at room temperature (for at least one month). However, it is rather unstable towards thermal energy, including milling.

During milling, gradual loss of ethanol may be observed. Drying such milled product, characterized in that the ethanol content is less than 0.4 molar equivalents, provides an ethanol-free aripiprazole, but this product is not identical with any of the known forms of solvent-free aripiprazole. It may be a mixture of Forms B and E, or a new form. Surprisingly, the mere drying of aripiprazole hemi-ethanolate at elevated temperatures (80-100° C. or more) provides a gradual loss of ethanol and the formation of aripiprazole Form B.

The chemical structure of aripiprazole methanolate is more complicated. In essence, the isolated crystals comprise, after drying at room temperature, essentially equimolar amounts of methanol and aripiprazole. The TGA shows that a part of methanol is bound quite firmly, while another part may be split more easily upon action of heat. In practice, the molar ratio between aripiprazole and methanol moieties in the isolated product is preferably from 1:0.6 to 1:1.2. Variations in the methanol content within the above ratios do not generally have an influence on the pattern of IR or x-ray powder diffraction spectra; i.e., the XRPD spectra may vary in peak intensities or in slight shifts of peaks, as is obvious in the art.

Aripiprazole methanolate is a crystalline substance having a specific IR spectrum and x-ray powder diffraction pattern different from any other known crystalline form of aripiprazole. Crystalline aripiprazole methanolate is more stable upon prolonged storage at room temperature than the hemi-ethanolate. Contrary to the hemi-ethanolate, aripiprazole methanolate does not change its crystalline structure during milling, even if a portion of the bound methanol is evaporated. However, prolonged drying at elevated temperatures, particularly at temperatures exceeding 80° C., result in desolvatation and the formation of aripiprazole Form B.

Aripiprazole hemi-ethanolate may be obtained by a crystallization of crude or conventional aripiprazole from ethanol, separating the obtained crystals from the liquid medium, such as by filtration or centrifugation, and drying the obtained wet product, preferably in vacuo, until the ethanol content is within the range of about 0.4 to 0.6 molar equivalent. To avoid breaking the solvate bonds, the temperature used for drying normally does not exceed 60° C.

Aripiprazole methanolate is obtainable by a crystallization of crude or conventional aripiprazole from methanol, and separating the obtained crystals from the liquid medium by filtration or centrifugation. To obtain a product free from unbound methanol, the process may be accompanied by a step of drying the obtained product, preferably at a temperature not exceeding 40° C., and generally in vacuo, until the methanol content drops to less than 1.2 molar equivalent.

The "crude/conventional aripiprazole" comprises any product comprising the compound 7-[4-[4-(2,3-dichlorophenyl)-1-piperazinyl]butoxy]-3,4-dihydrocarbostyril. For example, any form of aripiprazole may be used as the starting material; i.e., an isolated or un-isolated crude product arisen from the synthesis of aripiprazole or an aripiprazole product already crystallized such as the Type I-III or Form B-G as made by the techniques disclosed in the art, including hydrated forms.

The crystallization from ethanol/methanol may be performed by any suitable crystallization technique. For example, the aripiprazole can be dissolved in ethanol while hot, followed by cooling, either spontaneous or controlled, to induce crystallization. Alternatively, crystallization can be induced with the aid of a contrasolvent. For example, the aripiprazole can be dissolved in ethanol while hot, combining a contrasolvent with the solution, optionally with cooling, before, during, or after the combining, to precipitate crystals. Suitable contrasolvent to ethanol is, e.g., heptane. The formed crystals may be isolated, preferably at a room temperature or lower, from the slurry by ordinary processes of filtration or centrifugation. If desired, the solid may be washed by the crystallization solvent. The unbound solvent may be, if necessary, removed by drying. In case of the hemi-ethanolate, the drying conditions should be selected in such a way that the temperature does not exceed 60° C. and the drying time is controlled in such a way that the content of ethanol in the product is between 0.4 to 0.6 molar equivalent of the aripiprazole.

The both solvates of the present invention may be converted into the non-solvated aripiprazole, particularly into form B aripiprazole. As used herein "Form B" of aripiprazole means a crystalline aripiprazole substance having an x-ray powder diffraction pattern that substantially corresponds to the Form B product as defined in WO 03/26659. "Substantially corresponds" is meant to cover variations/differences in the pattern that would not be understood by a worker skilled in the art to represent a difference in crystal structure, but rather differences in technique, sample preparation, impurities, etc. Typically the Form B aripiprazole will have a single melting endotherm peak within the range of 138 to 144° C., especially 139-141° C., measured using differential thermal analysis (DTA) or differential scanning calorimetry (DSC). While in theory the values should correspond to the values recited in WO 03/26659, the DTA and DSC values should be used with a certain care as these types of data are dependant on measuring conditions such as heating rate, type of equipment, sample purity, sample loading, etc. Indeed, it is even possible for a Form B aripiprazole, as defined above, to exhibit two endothermic peaks.

The conversion can be thermally induced by heating as mentioned above or by a re-crystallization from a suitable solvent selected from 1-propanol, 2-propanol, 1-butanol, acetonitrile, ethyl acetate, or combinations thereof, as is more fully explained in U.S. Provisional Application 60/628,653, filed Nov. 18, 2004, the entire contents of which are incorporated herein by reference. Generally, the ratio of components within the mixture(s) is not particularly limited. Normally the solvent is anhydrous, i.e. traces of water ordinarily present in conventional batch should be controlled and, if necessary, removed. Typically the water content within the solvent system is less than 1%. The crystallization of aripiprazole as Form B is carried out in the above solvent, using crystallization techniques generally known in the art. Typically the solvent is heated in order to increase the solubility of the aripiprazole. The crystallization process may be induced or aided by adding small amounts of seed crystals of aripiprazole Form B. The conditions of crystallization (concentration, cooling rate) are advantageously adjusted in such a way that crystals become separated from the solution at a temperature less than 65° C.

Similarly, an aripiprazole hydrate, specifically the aripiprazole Form A may be obtained by crystallizing the aripiprazole alcoholates of the present invention from a solvent comprising water. Typically, such solvent is an ethanol/water mixture. The conditions of crystallization are, mutatis/mutandis, similar as disclosed above. As used herein "Form A" of aripiprazole means a crystalline aripiprazole substance having an x-ray powder diffraction pattern that substantially corresponds to the Form A product as defined in WO 03/26659.

The aripiprazole methanol and ethanol solvates of the present invention can also be formulated into a pharmaceutical composition, especially a solid oral dosage form such as a tablet or capsule, by combining the same with one or more pharmaceutically acceptable excipients. Generally the amount of aripiprazole, calculated as a solvent-free product, is within the range of 1 to 50 mg per unit dose, and specially 2, 5, 10, 15, 20, 25, or 30 mg per tablet. The choice of excipients is not particularly limited.

In one embodiment, the aripiprazole alcoholate is formed into granules with at least one granulateable binder. The granulating can be carried out by any known technique and generally comprises combining the aripiprazole alcoholate, a granulateable binder, and optionally a granulation liquid, and granulating the mixture to form granules. The granules can be dried. In one embodiment, the drying is carried out under sufficiently high temperature conditions and duration that the aripiprazole alcoholate is converted to a solvate-free aripiprazole and preferably is converted to aripiprazole Form B.

The present invention is more particularly described and explained by the following examples. It is to be understood, however, that the present invention is not limited to these examples and various changes and modifications may be made without departing from the scope of the present invention.

EXAMPLE 1

Hemi-ethanolate 1.0 g of aripiprazole was dissolved in 100 ml of ethanol at reflux. The solution was allowed to cool to room temperature (R.T.) in an open flask. During 24 hours at R.T. crystals were formed. The crystals were isolated by filtration over a P3-glass filter (reduced pressure) and air dried at R.T. for 2 hours. Thin plate-like crystals with a yield of 500 mg were obtained.

DSC: (melting) peak around 96-100 with irregular shoulder in front of the peak. Furthermore, melting around 138-140° C. and a tiny peak around 148-150° C.

NMR: Approximately 0.5 equivalent of ethanol present.

TGA: Complex stepwise mass loss between 75-100° C. (about 5.5% mass) and gradual mass loss above 220° C. (thermal degradation). The step size corresponds with 0.53 molar equivalent of ethanol.

EXAMPLE 2

Hemi-ethanolate 1.0 g of aripiprazole was dissolved in 15 ml of ethanol at reflux. The hot solution was added to 15 ml of cold n-heptane, stirred at 0° C. in an ice-water bath. After a few seconds, a white suspension was formed. The suspension was stirred at 0° C. for a few minutes. The solid was collected by filtration on a glass filter (vacuum) and air dried overnight at R.T. A white, crystalline powder was obtained. The yield was 920 mg.

DSC: (evaporation) peak between 75-100° C. Large melting peak around 138-140 C and tiny melting peak around 148-150° C. Comparable with DSC scan of Example 1.

NMR: Approximately 0.5 equivalent of ethanol present.

TGA: Stepwise mass loss between 75-95° C. (about 5.0% mass) and gradual mass loss above 220° C. (thermal degradation). The step size corresponds with 0.49 molar equivalent of ethanol, XRPD: Essentially similar to that of Example 3.

EXAMPLE 3

Hemi-ethanolate 30.0 g of aripiprazole was dissolved in 450 ml of ethanol at reflux using an oil bath. Reflux was maintained for about 30 minutes, while the solution was stirred with a magnetic stirrer. The hot solution was slowly cooled to room temperature taking about 3 hours. During cooling, crystallization occurred. The suspension was chilled at 0° C. and stirred at 0° C. for about 45 minutes. The crystals were isolated by filtration over a P3-glass filter (reduced pressure) and air-dried overnight at R.T. Colorless and shiny crystals with a yield of 30.36 g were obtained.

Figure 4:
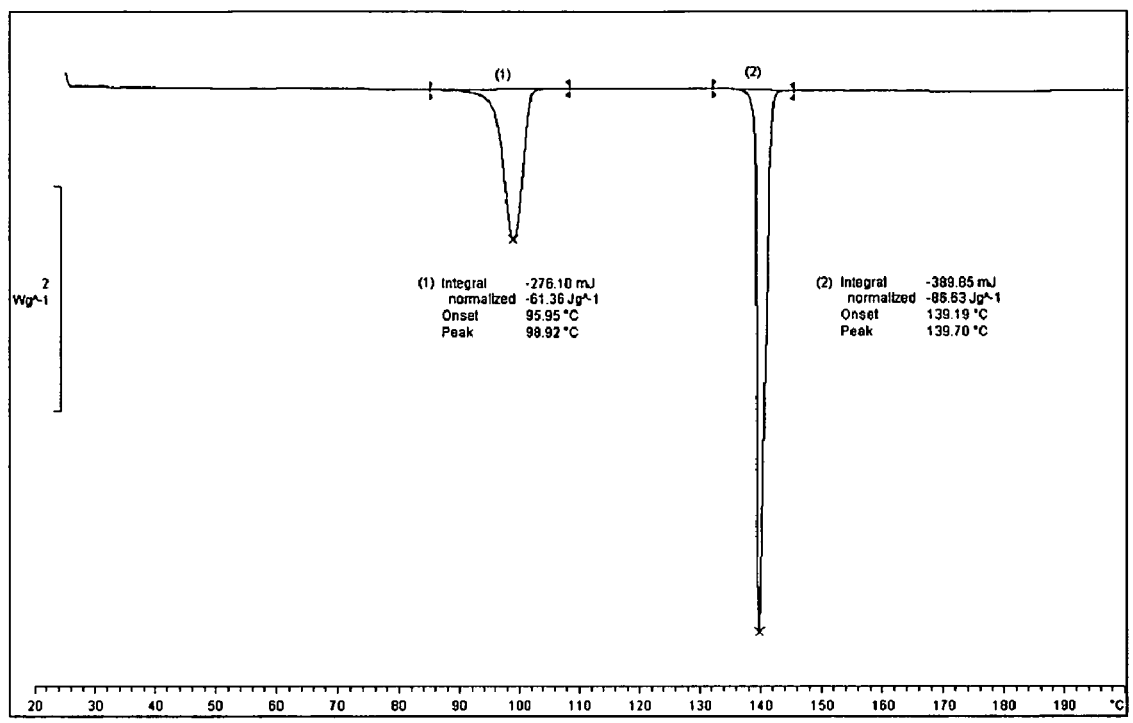
FIG. 4 represents a DSC curve of aripiprazole hemi-ethanol solvate of Example 3.

DSC: See FIG. 4, peak around 96-99° C. and melting peak around 139-140° C.

Figure 5:
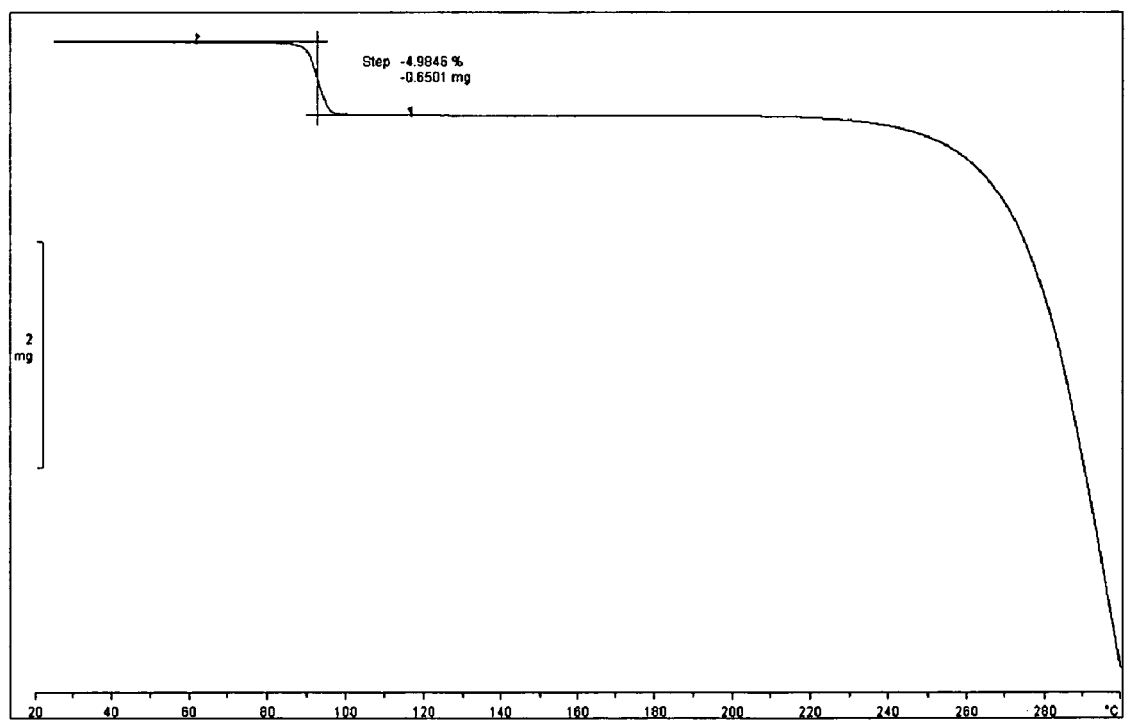
FIG. 5 represents a TGA curve of aripiprazole hemi-ethanol solvate of Example 3.

TGA: See FIG. 5, mass loss between 80-95° C. (about 5.0% mass, 0.5 mol. eq. of ethanol) and gradual mass loss above 220° C. (thermal degradation).

Figure 3:
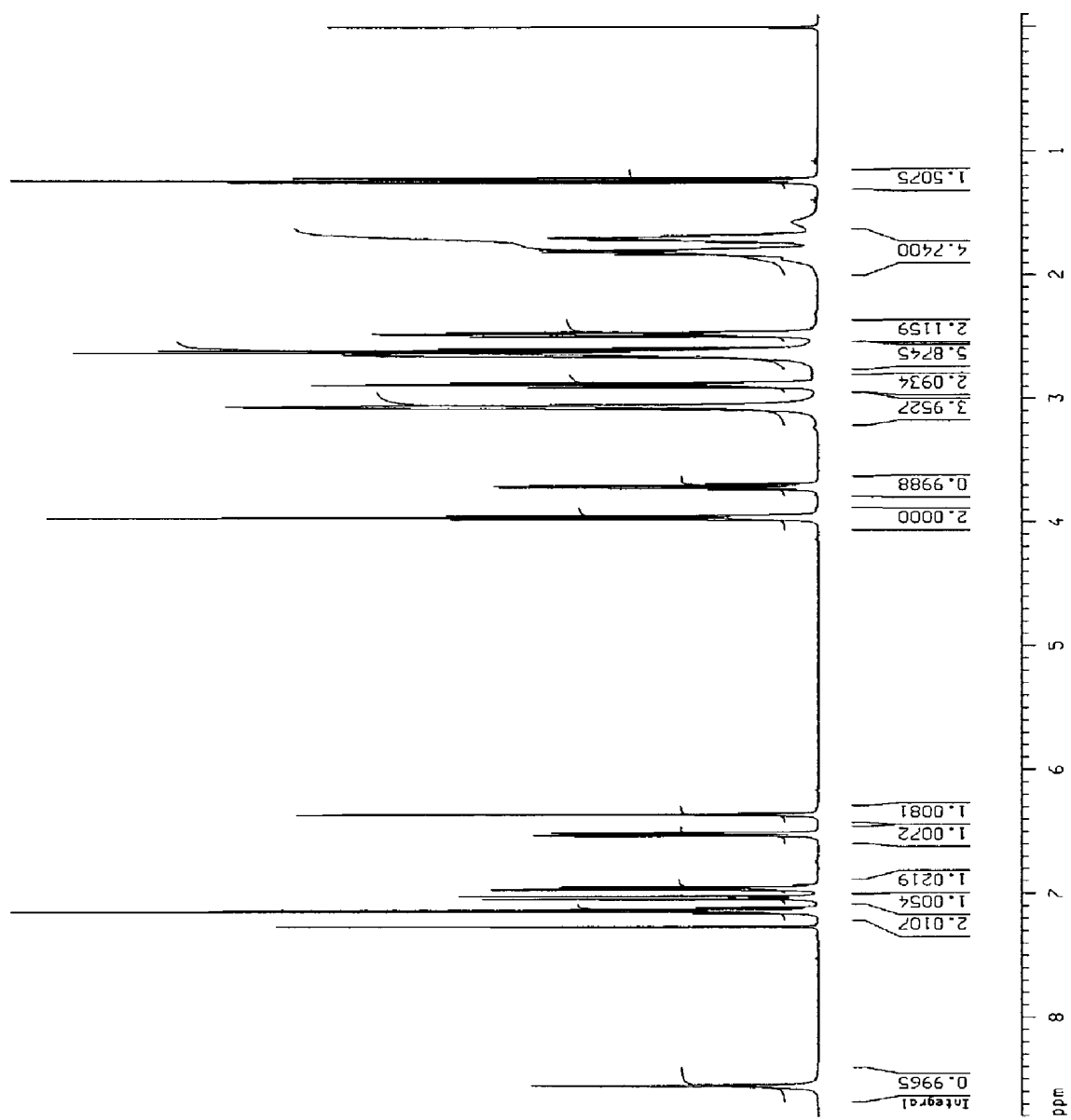
FIG. 3 represents a NMR spectrum of aripiprazole hemi-ethanol solvate of Example 3.

NMR: See FIG. 3, approximately 0.5 equivalent of ethanol present.

KF: No water present.

IR: See FIG. 1.

Figure 2:
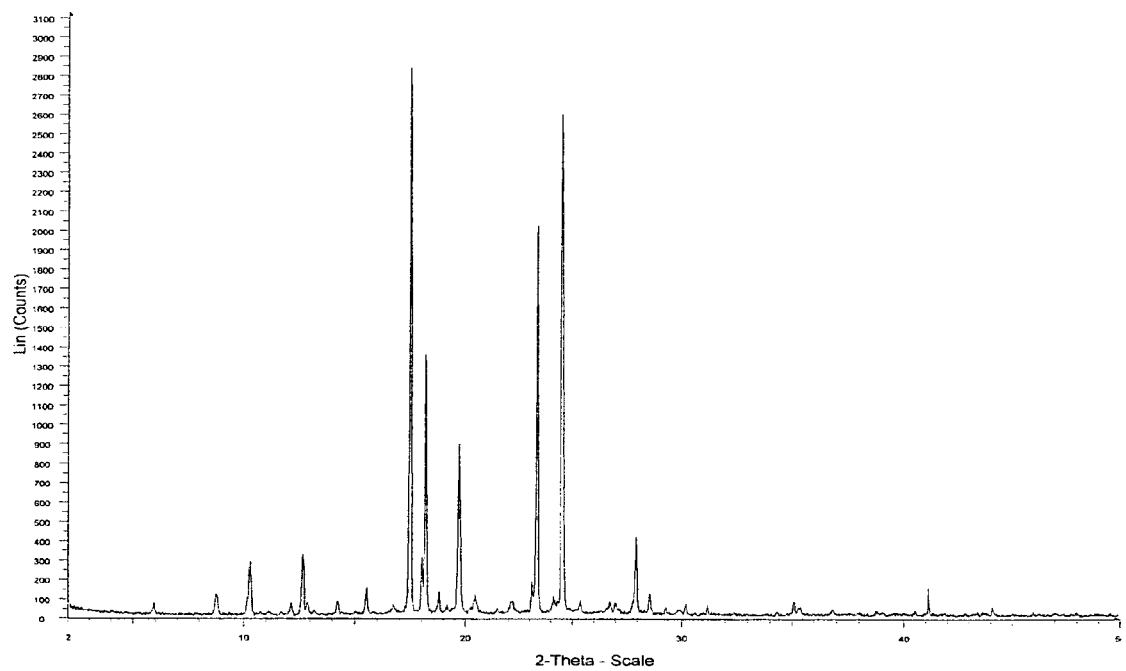
FIG. 2 represents an XRPD pattern of aripiprazole hemi-ethanol solvate of Example 3.

XRPD: See FIG. 2.

HSM: Somewhat blocky, prism-like crystals. Crystal size is typically between 100-300 μm, preferably between 100-200 μm.

Conversion Studies:

The above product was milled with a Fritsch Pulverisette 14 rotation miller. A 0.08 mm pore size sieve was used and the rotation speed was set to 6000 rpm. The obtained powder was not sticky, but there was a stronger smell of ethanol detectable. The milled product was stored overnight at RT in a closed bottle.

DSC: Broad evaporation peak between 55-100° C., melting peak around 138-140° C., recrystallization between 140-146° C. and melting around 148-150° C.

TGA: Broader evaporation step between 25-95° C. (about 3.6% mass, 0.35 mol. eq. of ethanol) and gradual mass loss above 220° C. (thermal degradation).

NMR: approximately 0.33 equivalent of ethanol present.
KF: No water present.
IR: Similar to the IR spectrum of the sample before milling
XRPD: Similar to the XRPD spectrum of the sample before milling. Few additional peaks could point to a trace of form E.
HSM: More irregular and opalescent particles. Opalescence is caused by crystal defects and cracks. Crystal size is typically between 50-150 µm, but also smaller fragments.

The milled product was then dried at 100° C. for 24 hours, giving the following analysis.
DSC: Three melting peaks around 138-140° C., 143-145° C. and 148-149° C. respectively. Recrystallization peaks between the melting peaks.
TGA: No mass loss up to 210-220° C., so no solvent or water was present any more.
NMR: No ethanol present.
KF: No water present.
IR: Different from the hemi-ethanolate. Different from form B.
XRPD: Shows features for both form B and form E.
HSM: Irregular and opalescent particles. Crystal size is typically between 30-150 µm, but also smaller fragments. Only a few particles larger than 150 µm.

EXAMPLE 4

100 g of aripiprazole was dissolved under reflux in 1500 ml of ethanol. The solution was allowed to cool to room temperature while being stirred. The suspension was further cooled to 0-5° C. by cooling in an ice-water bath. The solid was collected by filtration and dried overnight in a vacuum oven at 80 C. DSC showed the hemi-ethanolate.

The sample was dried at 80° C. and under vacuum for an additional 4 days. DSC showed that the substance still contains some hemi-ethanolate.

The substance was therefore dried overnight at 90° C. and under vacuum. The extra dried material DSC showed a trace of the hemi-ethanolate left.

Finally, the substance was dried at 100° C. and under vacuum for 2 days. After this drying step at 100° C., the drug substance was analyzed by DSC and XRPD, which showed pure Form B aripiprazole.

EXAMPLE 5

Hemi-ethanolate 30.03 g of aripiprazole was dissolved in 450 ml of ethanol at reflux using an oil bath. Reflux was maintained for about 2 hours, while the solution was stirred with a magnetic stirrer. The hot solution was cooled to room temperature taking about 1 hour. Crystallization already started after a few minutes. The suspension was chilled at 0° C. and stirred at 0° C. for about 30 minutes. The crystals were isolated by filtration over a P3-glass filter (reduced pressure) and air-dried overnight at R.T. Colorless and shiny crystals with a yield of 29.66 g were obtained.
TGA: approximately 4.9 mass %=0.5 equivalent of ethanol present.
NMR: approximately 0.5 equivalent of ethanol present.
IR: Corresponds to the hemi-ethanolate.
XRPD: Corresponds to the hemi-ethanolate.
HSM: Well defined and transparent parallelepiped-like, trapezium-like or prism-like crystals (thick plates). Crystal size is typically between 100-300 µm, preferably between 200-300 µm.

Sieving
The above product was forced sieved through a 100 µm sieve. This forced sieving was applied by pressing the drug substance through the sieve using a spatula. The obtained finer powder yielded the following analysis.
TGA: approximately 4.8 mass %=nearly 0.5 equivalent of ethanol present.
IR: Similar to the IR spectrum of the sample before forced sieving
XRPD: Similar to the XRPD spectrum of the sample before milling. No indications for traces of another form.
HSM: More irregular and less transparent particles (crystal fragments). Opalescence is caused by crystal defects, cracks and tiny particles on the larger crystal fragments. Crystal size is below 120 µm.
Conclusion/discussion: Forced sieving has no detectable effect on the crystal structure.

Drying
The sieved product was dried overnight at 40° C., overnight at 60° C., and dried at 80° C. for 6 days. During drying, vacuum was applied.
TGA: approximately 0.06 mass % of ethanol present.
XRPD: Form B

EXAMPLE 6

Figure 7:
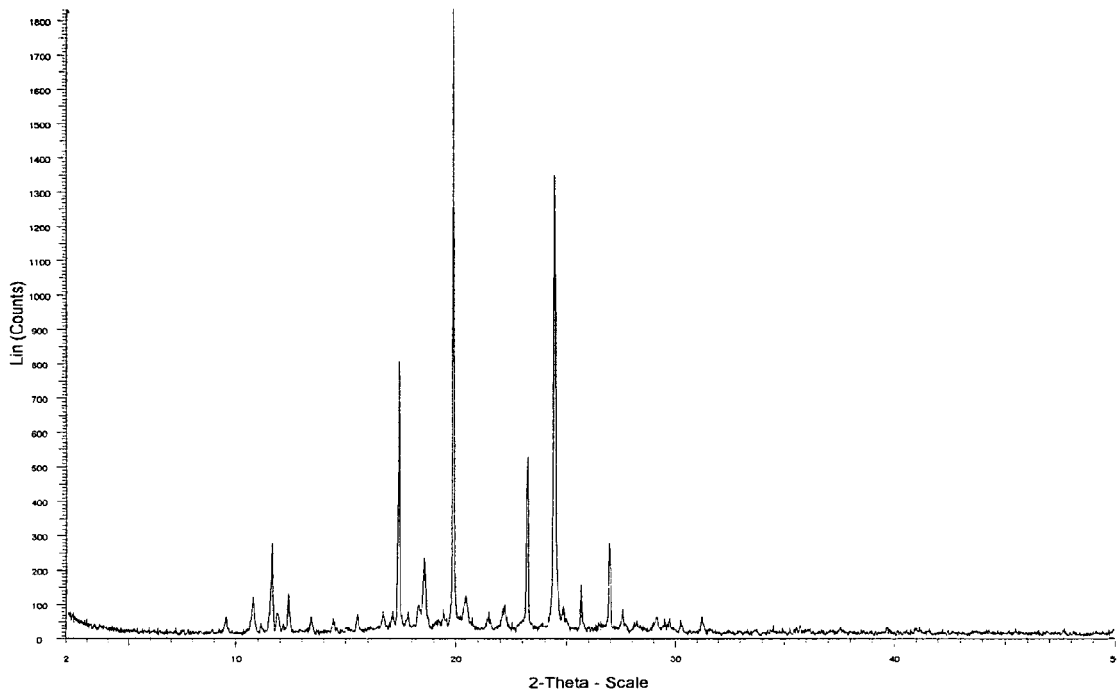
FIG. 7. represents an XRPD pattern of aripiprazole methanol solvate of Example 6.
Figure 6:
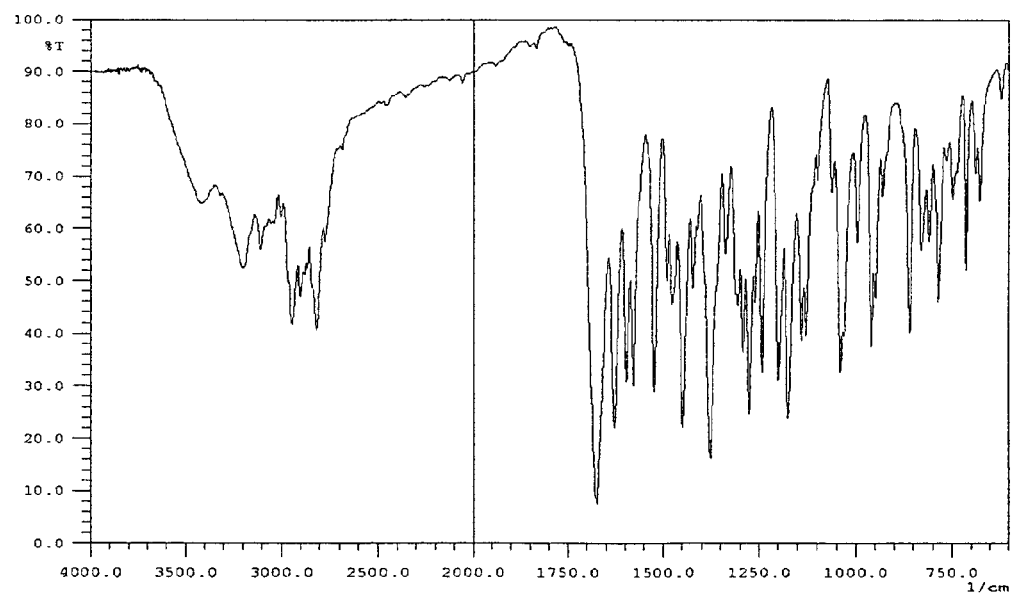
FIG. 6. Represents an IR spectrum of aripiprazole methanol solvate of Example 6.
Figure 8:
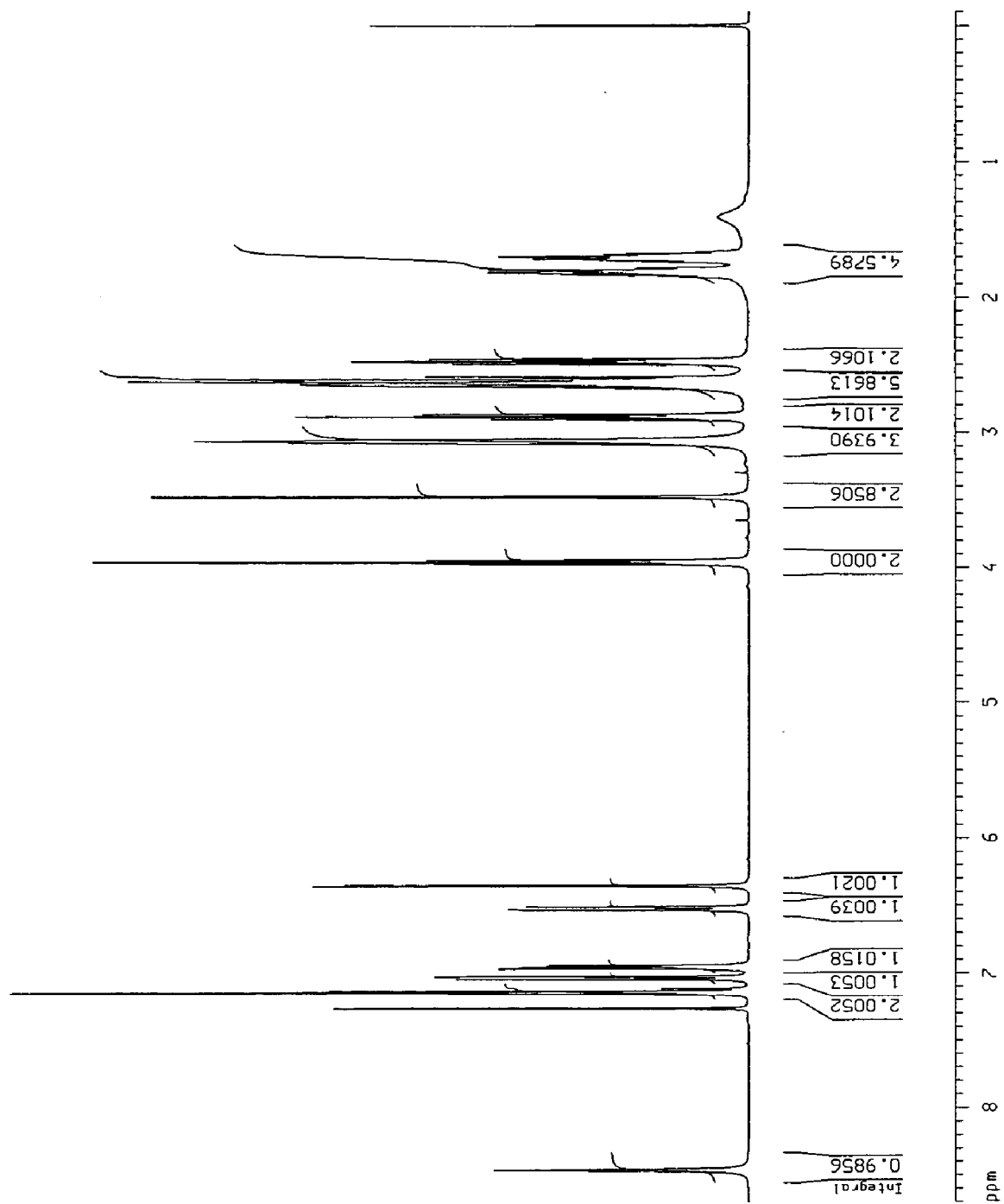
FIG. 8. represents a NMR spectrum of aripiprazole methanol solvate of Example 6.
Figure 9:
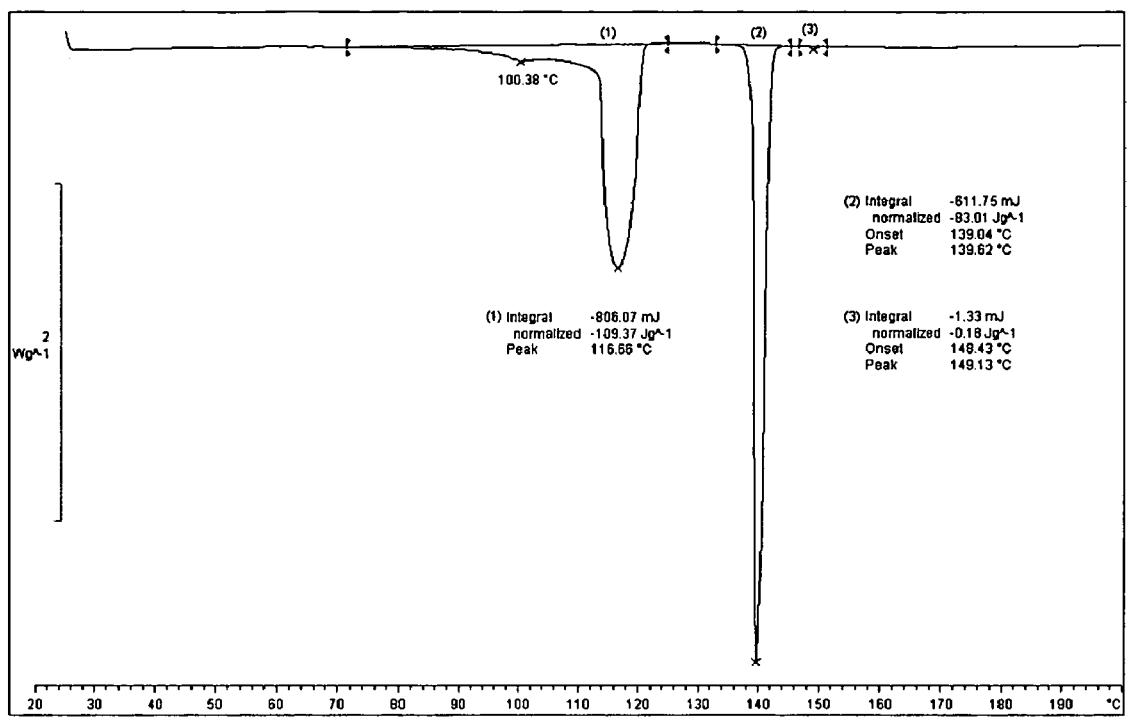
FIG. 9. represents a DSC curve of aripiprazole methanol solvate of Example 6.
Figure 10:
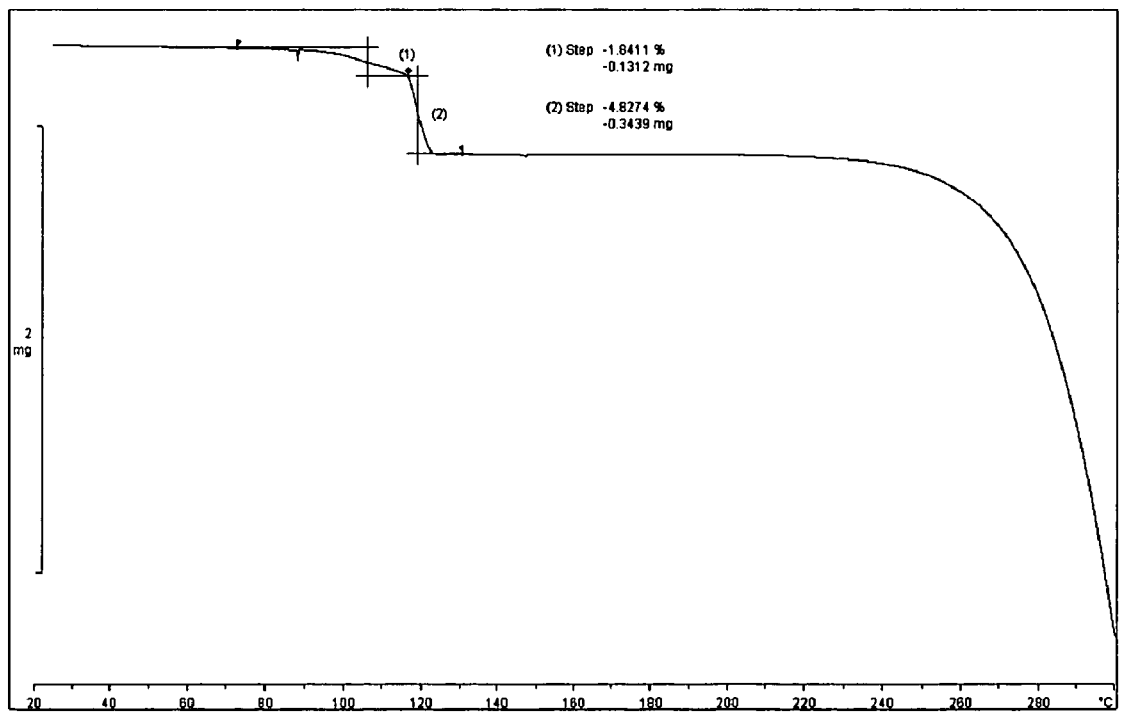
FIG. 10. represents a TGA curve of aripiprazole methanol solvate of Example 6.

Methanolate 1.01 g of aripiprazole was dissolved in 160 ml of methanol at reflux. The hot solution was allowed to cool to room temperature and left at R.T. for 1.5-2 hours. Crystallization started after 15 minutes and appeared to be completed after 30 minutes. The crystals were isolated by filtration over a P3-glass filter (reduced pressure) and air dried overnight at R.T. Colorless, shiny crystals (needles/plates) were obtained. The yield was 740 mg.
DSC: See FIG. 9
NMR: See FIG. 8. Almost 1.0 equivalent of methanol present.
TGA: See FIG. 10. Two steps of mass loss between 75-120° C. The total size of both steps together corresponds with 0.94 equivalent of methanol.
XRPD: See FIG. 7. Does not correspond to the XRPD spectra of any of the prior art forms
IR: See FIG. 6.
HSM: Long plate-like and needle-like crystals, often well defined. Crystal lengths are up to a few mm. Some internal structures and lines visible. Upon heating, little escape of solvent visible, slowly increasing with increasing temperature. Escape of solvent becomes more distinct above 80° C. (change of color and brightness, darkening, cracking). In addition, a transition is visible as new small crystals develop within the existing crystals. Between 110-118° C. severe cracking due to the escape of methanol; crystals become opaque. All crystals melt above 138° C.

Conversion to Form B:
The crystals were milled for 1 minute in a Fritsch pulverisette 23, ball mill. The frequency was set to 30 oscillations/sec and one agate ball (diameter of about 0.5 cm) was used. Subsequently, the milled sample was dried at 100° C. for 24 hours.
DSC: melting peak around 139-140° C. and a tiny peak around 148-150° C.
TGA: No mass loss up to 210° C.
NMR: No methanol left.
KF: No water present
IR: Corresponds to Form B.

XRPD: Corresponds to Form B. No indications of traces of the methanolate or any other forms.

HSM: Irregular and opalescent crystal particles. Crystal size is typically between 50-100 μm.

EXAMPLE 7

Methanolate 5.0 g of aripiprazole (GE.SNO31201.041012.01) was dissolved in 800 ml of methanol at reflux using an oil bath. Reflux was maintained for about 30 minutes, while the solution was stirred with a magnetic stirrer. The hot solution was cooled to room temperature taking about 1.5 hours. Crystallization started after approximately 30 minutes. The suspension was chilled at 0° C. and stirred at 0° C. for about 1.5 hours. The crystals were isolated by filtration over a P3-glass filter (reduced pressure) and air-dried overnight at R.T. Colorless and shiny crystals with a yield of 4.75 g were obtained.

DSC: Broad evaporation peak between 80-120° C. with a sharp embedded peak with a peak maximum of 115.4° C. Melting peak around 139-140° C.

TGA: Two steps between 70-110° C. (2.0 mass % and 4.3 m % respectively). Correspond to 0.28+0.60=0.88 equivalent of methanol.

NMR: Almost 1 equivalent of methanol present.
IR: Similar to the IR spectrum of Example 6.
XRPD: Comparable to the XRPD spectrum of Example 6.
Milling A small portion was milled for 1 minute in a Fritsch pulverisette 23, ball mill. The frequency was set to 30 oscillations/sec and one agate ball (diameter of about 0.5 cm) was used. Subsequently, the milled sample was kept overnight at R.T. in a closed bottle.

DSC: Broad evaporation peak between 25-115° C. with a sharp embedded peak with a peak maximum of 114.4° C. Melting peak around 139-140° C. Tiny peak around 148-150° C.

TGA: Stepwise mass loss between 25-110° C. (5.0 m %). Correspond to 0.70 equivalent of methanol.

NMR: Almost ⅔ equivalent of methanol present.
IR: Similar to the IR spectrum of before milling.
XRPD: Similar to the XRPD spectrum before milling. Some differences in peak intensities can be attributed to preferred orientation.

Conclusion/discussion: A similar IR spectrum and XRPD spectrum show that the crystal structure has not been changed by milling. XRPD shows no traces of other forms.

EXAMPLE 8

Monohydrate 10.0 g of aripiprazole was dissolved in 200 ml of ethanol/water (4:1 v/v) at reflux using an oil bath. Reflux was maintained for about 30 minutes, while the solution was stirred with a magnetic stirrer. The hot solution was cooled to room temperature taking about 1 hour. Crystallization started already after a few minutes. The suspension was chilled at 0° C. and stirred at 0° C. for about 30 minutes. The crystals were isolated by filtration over a P3-glass filter (reduced pressure), dried at 50° C. for 2 hours and dried overnight at R.T. Colorless and shiny crystals with a yield of 9.60 g were obtained.

DSC: Broad evaporation peak between 55-125° C. with a sharp embedded peak with a peak maximum of 124.2° C. Melting peak around 139-140° C. Small melting peak around 148-150° C.

TGA: Approximately 4.0 mass %=1.0 equivalent of water present.
NMR: Only water present.
IR: Corresponds to Form A.
XRPD: Corresponds to Form A.

EXAMPLE 9

1.01 g of aripiprazole hemi-ethanolate was dissolved in 15 ml of ethyl acetate at reflux using an oil bath and under stirring. About 5 ml of ethyl acetate was evaporated at reflux using a Dean-Stark apparatus. The hot solution was slowly cooled to R.T. taking about 1.5 hours, stirring was continued. During cooling, slow crystallization occurred. The suspension was chilled at 0° C. and stirred at 0° C. for 15 minutes. The crystals were isolated by filtration over a P3-glass filter (reduced pressure) and dried overnight at 40° C. and under vacuum. Colorless, shiny, flake-like crystals with a yield of 830 mg were obtained.

DSC: Melting peak around 139-141° C.
TGA: No significant mass loss up to 210° C. detected. Gradual mass loss above 210° C. (thermal degradation).
IR: Corresponds to Form B.
XRPD: Corresponds to Form B.

EXAMPLE 10

1.0 g of aripiprazole methanolate was dissolved in 15 ml of ethyl acetate at reflux using an oil bath and under stirring. About 5 ml of ethyl acetate was evaporated at reflux using a Dean-Stark apparatus. The hot solution was slowly cooled to R.T. taking about 1-1.5 hours, stirring was continued. During cooling, slow crystallization occurred. The suspension was chilled at 0° C. and stirred at 0° C. for 15 minutes. The crystals were isolated by filtration over a P3-glass filter (reduced pressure) and dried overnight at 40° C. and under vacuum. Colorless, shiny, flake-like crystals with a yield of 780 mg were obtained.

DSC: Melting peak around 139-140° C.
TGA: No significant mass loss up to 220° C. detected. Gradual mass loss above 210° C. (thermal degradation).
IR: Corresponds to Form B.
XRPD: Corresponds to Form B.

EXAMPLE 11

1.0 g of aripiprazole hemi-ethanolate was dissolved in 20 ml of ethanol/water (4:1 v/v) at reflux using an oil bath. Reflux was maintained for about 20 minutes, while the solution was stirred with a magnetic stirrer. The hot solution was slowly cooled to room temperature taking about 1.5 hours. Crystallization occurred during cooling. The suspension was chilled at 0° C. and stirred at 0° C. for about 1 hour. The crystals were isolated by filtration over a P3-glass filter (reduced pressure), dried at 50° C. for 2 hours and dried overnight at R.T. A white, crystalline powder with a yield of 860 mg was obtained.

DSC: Broad evaporation peak between 55-125° C. with a sharp embedded peak with a peak maximum of 124.1° C. Melting peak around 139-140° C.

TGA: Approximately 4.0 mass %=1.0 equivalent of water present.
IR: Corresponds to Form A.
XRPD: Corresponds to Form A.

EXAMPLE 12

1.0 g of aripiprazole methanolate was dissolved in 20 ml of ethanol/water (4:1 v/v) at reflux using an oil bath. Reflux was maintained for about 45 minutes, while the solution was stirred with a magnetic stirrer. The hot solution was slowly cooled to room temperature taking about 2 hours. Crystallization occurred during cooling. The suspension was chilled at 0° C. and stirred at 0° C. for about 1 hour. The crystals were isolated by filtration over a P3-glass filter (reduced pressure), dried at 50° C. for 2 hours and dried overnight at R.T. A white, crystalline powder with a yield of 850 mg was obtained.

DSC: Broad evaporation peak between 60-130° C. with a sharp embedded peak with a peak maximum of 124.0° C. Melting peak around 139-140° C.

TGA: approximately 3.9 mass %=1.0 equivalent of water present.

IR: Corresponds to Form A.

XRPD: Corresponds to Form A.

Each of the patents and journal articles mentioned above are incorporated herein by reference. The invention having been described it will be obvious that the same may be varied in many ways and all such modifications are contemplated as being within the scope of the invention as defined by the following claims.

We claim:

1. An alcoholate of aripiprazole, wherein said alcoholate is aripiprazole hemi-ethanolate.

2. The alcoholate according to claim 1, wherein said alcoholate is substantially free from unbound solvent.

3. The alcoholate according to claim 1, which is crystalline hemi-ethanolate having a molar ratio of ethanol to aripiprazole within the range of 0.45:1 to 0.6:1, respectively.

4. A pharmaceutical composition comprising an aripiprazole alcoholate according to claim 1 and at least one pharmaceutically acceptable excipient.

5. The pharmaceutical composition according to claim 4, wherein said composition is a solid oral dosage form.

6. A granulate, comprising granules containing an aripiprazole alcoholate according to claim 1 and at least one granulateable binder.

7. A process for making aripiprazole Form B, which comprises heating an aripiprazole alcoholate selected from aripiprazole hemi-ethanolate and aripiprazole methanolate to form aripiprazole Form B.

8. The process according to claim 7, wherein said alcoholate is aripiprazole methanolate.

9. The process according to claim 8, which further comprises milling said aripiprazole methanolate prior to said heating step.

10. A process for making a pharmaceutical granulate, which comprises:
granulating a mixture of a granulateable binder, an aripiprazole alcoholate selected from hemi-ethanolate and methanolate, and optionally a granulating liquid, to form granules; and
drying said granules, wherein said drying converts said aripiprazole alcoholate into a non-solvated aripiprazole.

11. The process according to claim 10, wherein said heating converts said aripiprazole alcoholate into aripiprazole Form B.

12. The process according to claim 7, wherein said alcoholate is aripiprazole hemi-ethanolate.

13. The process according to claim 12, wherein said aripiprazole hemi-ethanolate is not milled prior to said heating step.

14. The process according to claim 7, wherein said heating includes reaching temperatures of at least 80° C.

15. The process according to claim 8, wherein said heating includes reaching temperatures of at least 80° C.

16. The process according to claim 12, wherein said heating includes reaching temperatures of at least 80° C.

* * * * *